United States Patent [19]

Park

[11] Patent Number: 5,343,877

[45] Date of Patent: Sep. 6, 1994

[54] ORTHOPEDIC IMPLANT AND METHOD

[75] Inventor: Joon B. Park, Coralville, Iowa

[73] Assignee: University of Iowa Research Foundation, Oakdale, Iowa

[21] Appl. No.: 942,515

[22] Filed: Sep. 9, 1992

[51] Int. Cl.$^5$ .................. A61B 19/00; A61F 2/32; A61F 2/30; A61F 2/28

[52] U.S. Cl. .................. 128/898; 128/897; 623/22; 623/18; 623/16; 606/53; 606/92

[58] Field of Search .............. 623/16, 18, 22, 11, 623/66, 20, 21, 23; 606/53, 60, 62, 76, 77, 86, 92, 93, 94, 95; 128/897, 898

[56] References Cited

U.S. PATENT DOCUMENTS

| | | |
|---|---|---|
| 4,202,055 | 5/1980 | Reiner et al. ............... 623/16 |
| 4,266,303 | 5/1981 | Park ............................ 623/16 |
| 4,281,420 | 8/1981 | Raab ........................... 3/1.912 |
| 4,365,357 | 12/1982 | Draenert ..................... 623/16 |
| 4,483,799 | 8/1981 | Pratt, Jr. et al. ............ 3/1.913 |
| 4,491,987 | 1/1985 | Park ............................ 3/1.91 |
| 4,843,112 | 6/1989 | Gerhart et al. ............. 523/114 |
| 5,061,286 | 10/1991 | Lyle ............................ 623/16 |

OTHER PUBLICATIONS

Oonishi, et al. "Interface Bioactive Bone Cement by Using PMMA and Hydroxyapatite Granules", Bioceramics (Proceedings of 1st International Bioceramic Symposium), 1989.

Primary Examiner—Randall L. Green
Assistant Examiner—Dinh X. Nguyen
Attorney, Agent, or Firm—Zarley, McKee, Thomte, Voorhees & Sease

[57] ABSTRACT

A process of orthopedic implantation of prosthetic devices such as hip and knee joints. The prepared bed of the bone cavity is lined with a pre-coating mixture of bone cement and resorbable particles, followed by filling of the bed with substantially pure bone cement and thereafter the prosthesis is positioned into the fully prepared bed. In this manner, resorbable particles along the lined prepared bed wall are resorbed by the patients body and replaced with new bone tissue ingrowth. As a result bonding of the bone cement to the bone is substantially improved, without weakening the bonding of the implant to the bone cement.

12 Claims, 2 Drawing Sheets

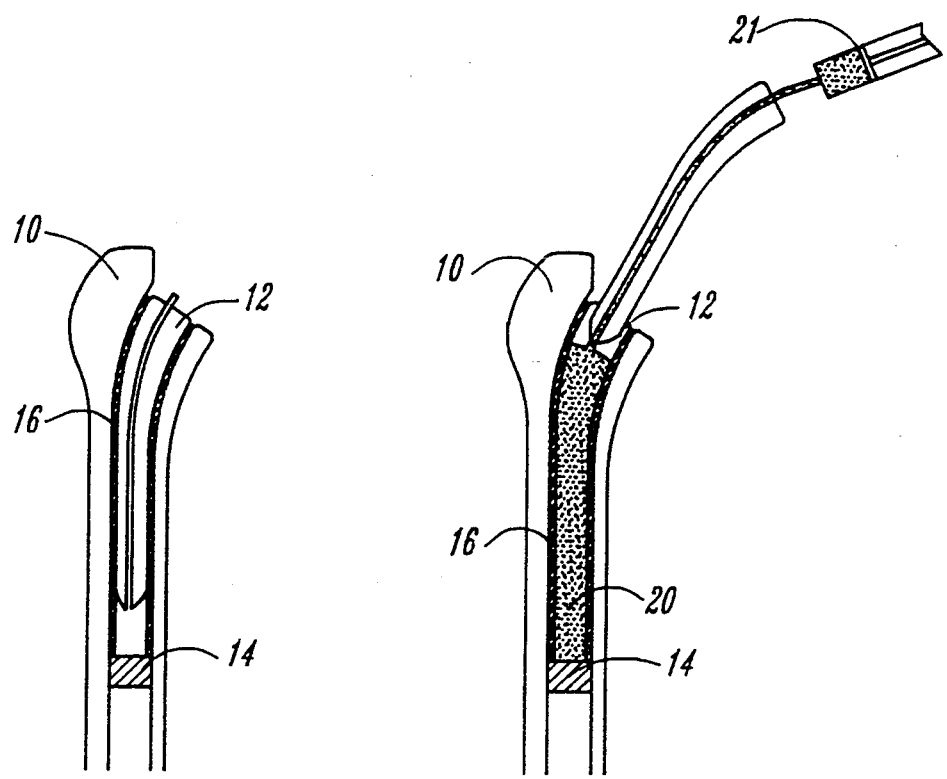
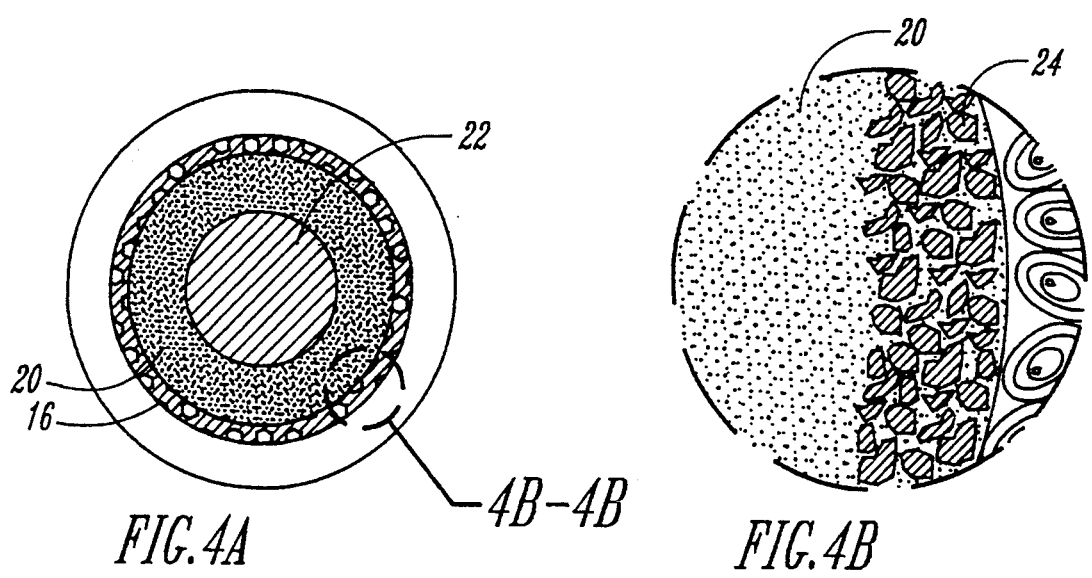

ORTHOPEDIC IMPLANT AND METHOD

BACKGROUND OF THE INVENTION

The present invention relates to orthopedic implantation, particularly implantation of prosthetic devices to repair or replace hard tissue of warmblooded mammals, e.g., bones and joints of humans and animals. The process utilizes a bone cement for fixation of the prosthesis.

One of the inherent problems of orthopedic implantation is the fixation and the maintenance of a stable interface between the device and the host tissue. Polymethylmethacrylate based bone cement has been widely used to fix the implant. The bone cement fixation creates two interfaces: cement/bone and cement/implant. According to an earlier report the incidence of loosening for the femoral prostheses of hip joint arthroplasties were evenly divided at about 10% and 11% for cement/implant and cement/bone interfaces, respectively. The cement/implant interface loosening can be minimized by pre-coating with bone cement or polymethylmethacrylate polymer. Pre-coating can achieve a good bonding between the "cement" and prosthesis during the manufacturing process. During surgery, the freshly doughed cement adheres well to the pre-coated cement.

The problems at the bone/cement interface cannot be easily overcome since these problems arise from the intrinsic properties of the bone cement as well as extrinsic factors such as cementing technique. The toxicity of the monomer, inherent weakness of the cement as a material, and inevitable inclusion of the pores can contribute to the problem of loosening at the bone/cement interface.

The bone/cement interface strength may be enhanced by the bone ingrowth into the cement. Bone cement can be used for immediate fixation yet provide tissue ingrowth space later by incorporating resorbable particles (such as demineralized or deproteinized bone).

In summary, potential advantages of the idea of using resorbable particle impregnated (polymethyl methacrylate) bone cement for the fixation of orthopedic implant for joint replacements are (1) Immediate fixation of the prosthesis and (2) Long term fixation of the prosthesis when the new tissues (bones) to replace the resorbable particles. However, there a are few inherent problems associated with the system: (1) The impregnation of the particles changes the physical properties for the worse in comparison with the original cement such as increased viscosity, making it difficult to mix and inject the cement, decreased mechanical strength, etc. (2) A more serious problem is the "unresorbable" particles due to the coating by the liquid monomer(methylmethacrylate) during mixing, which will result in preventing the resorption of particles. Earlier experiments on the bone morphogenic protein (BMP) resorbable particle impregnated cement did not fare as well as expected due to this problem.

A previous invention of mine relates to pre-coating of the prosthetic implant with bone cement composition in an effort to improve the bond at the interface of the implant and the bone cement composition, see Park, U.S. Pat. No. 4,491,987 issued Jan. 9, 1985 and entitled METHOD OF ORTHOPEDIC IMPLANTATION AND IMPLANT PRODUCT. The process and implant there described has met with a reasonable degree of success. However, this prior invention deals with the interface of the implant and the bone cement. There is also another interface of serious concern, namely, the interface of the bone and the bone cement. This interface is along the cavity made in the bone adapted for receipt of the implant. Typically, this cavity is referred to as the "prepared bed". The concept of placing resorbable particles in the bone cement composition so that the body of the patient resorbs the particles, leaving a porous structure for new bone growth tissue, is known. However, the prior practices involve mixing resorbable particles with the entire bone cement composition. This has some inherent problems in that it substantially weakens the cement, particularly with regard to the relationship of the bonding cement to the implant.

The present invention involves elimination or decrease of the problems associated with the bone cement fixation of a prosthesis by using resorbable particle delivering systems to allow the advantages of strong bond between pure bone cement and the implant, and at the same time, allows the advantages of strong bonding between the bone and a mixture of bone cement and resorbable particles. As a result, adjacent to the interface between the bone and cement, resorbable particles are resorbed over time and replaced with new ingrown bone tissue, further enhancing the bonding at this interface.

Accordingly, it is a primary objective of the present invention to provide an improved delivery system for inserting into patients prosthetic devices which must be fixed to the patients bone by a cement fixation process.

Another object of the present invention is to provide a delivery system which allows all of the advantages of the pure cement bonding to the implant, and as well, all of the advantages of bonding of a cement resorbable particle composition in the interface of the patient's bone in the prepared bed of the bone.

A yet further object of the present invention is to provide numerous delivery systems which accomplish each of the above achieved objectives.

The method and manner of accomplishing all of the above objectives, as well as others, will become apparent from the detailed description of the invention which follows hereinafter.

SUMMARY OF THE INVENTION

An improved prosthesis fixation for surgical implantation and an improved process for accomplishing the implantation is disclosed. In the process, the surface of the prepared bed of a bone cavity is lined with a composition mixture of bone cement and body resorbable particles. Thereafter, the remainder of the prepared bed is filled with substantially pure bone cement composition and the prosthesis is inserted into its correct position. In this manner the bond at the interface of the prosthesis and the bone cement is a bond between the prosthesis and substantially pure bone cement. On the other hand, the bond at the interface of the bone and the bone cement composition, is bond between bone cement and body resorbable particles which eventually are resorbed and replaced with new ingrown bone tissue ingrowth to strengthen the bond at this interface.

BRIEF DESCRIPTION OF THE DRAWINGS

FIGS. 3a and 3b an alternative method of insertion using an undersized template which may be gradually removed while simultaneously using injection insertion of bone cement.

FIGS. 4a and 4b illustrate the microstructure of the interface between the bone and the bone cement.

DETAILED DESCRIPTION OF THE INVENTION

Figure 1A:
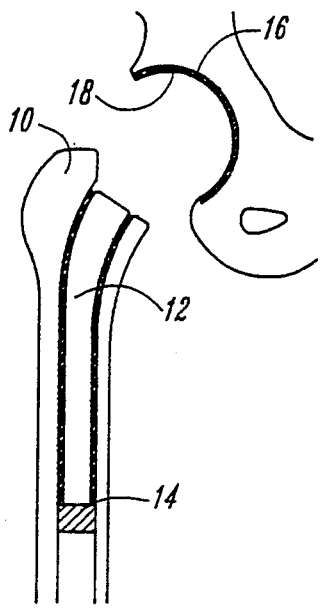
FIGS. 1a, 1b and 1c show a method of placement of a bone segment cement plug and a resorbable particle lining in the prepared bed, followed by placement of the bone cement and lastly (in FIG. 1c), insertion of the prosthesis.

The present invention relates to orthopedic implantation of prosthesis, utilizing bone cement as a fixative for the implant. The prosthesis to be implanted may be hip prosthesis, finger prosthesis, knee prosthesis, etc. The process of the present invention has usefulness for any type of prosthesis which involves on the one hand, an interface between the prosthetic device (metal) and a bone cement and, on the other hand, an interface between bone and the bone cement. The process involves the concept of providing and interface and bonding between both surfaces, which maximizes the opportunity for a strong, and hopefully, life-long bond between each.

Much has been reported about the use of bone cement for fixation of a prosthesis during an operative implantation procedure. During polymerization of methyl methacrylate monomer of the bone cement, present in both commercially approved versions of same in the United States, hoop stress develops in the bone cement due to shrinkage of the polymer. Depending upon the particular polymer and the amount of it utilized, hoop stress in the polymer can be of sufficient magnitude to create cracks in the bone cement layer and/or to create microscopic and macroscopic separations between the bone cement and the bone surface. The degree of shrinkage of the cement is proportional to the amount of new bone cement used during the operative procedure. Utilizing techniques of the present invention where a pre-coated prosthesis is utilized, a lesser amount of new bone cement is required, thus reducing polymer shrinkage and therefore hoop stress in the polymerized bone cement.

One commercially approved self-curing, bone cement composition, SURGICAL SIMPLEX® P, manufactured by Howmedica, Inc., Rutherford, N.J., is a two component system which includes a powder, 16.7 weight percent polymethyl methacrylate and 83.3 weight percent methyl methacrylate-styrene copolymer, and a liquid, 97.4 volume percent of methyl methacrylate monomer, 2.6 volume percent of N, N-dimethyl-p-toluidine and 75 plus or minus 15 parts per million of hydroquinone. If radio opacity is desirable for the bone cement, the powder component includes 15 weight percent polymethyl methacrylate, 75 weight percent methyl methacrylate-styrene copolymer and 10 weight percent of barium sulfate. A further commercially approved self-curing bone cement is manufactured by Zimmer U.S.A., Warsaw, Ind. and is likewise a two component system. The powder includes 99.25 weight percent of polymethyl methacrylate and 0.75 weight percent of benzoyl peroxide or, if radio-opacity is desired, 89.25 weight percent of polymethyl methacrylate, 10 weight percent of barium sulfate, and 0.75 weight percent of benzoyl peroxide. The liquid component includes 97.25 volume percent of methyl methacrylate monomer, 2.75 volume percent of N, N-dimethyl-p-toluidine and 75 plus or minus 10 parts per million of hydroquinone. While the two bone cements set forth above are the only two presently approved by the Food and Drug Administration for use in the United States, obviously other chemical compositions could likewise be suitable and should be considered to be within the purview of the present invention.

For implantation use, the two components of the bone cement are mixed and kneaded until a doughy consistency is obtained. A mixing-kneading time of at least four minutes is recommended to reduce the amount of free monomer that can be absorbed into the patient's bloodstream. The doughy cement is immediately forced into the bone cavity that has been prepared to receive the prosthesis. In the sense of cancellous bone structure, the bone cement is forced into the cavity with adequate pressure to place the doughy mixture within the interstices of the bone to provide a good physical interlock between the bone cement and the bone after curing of the bone cement. Subsequent to placement of the doughy mixture of bone cement composition within the prepared bone cavity, in accordance with my earlier invention, the prosthesis is wiped along the pre-coated surface of same with methyl methacrylate monomer and the prosthesis is then properly located within the bone cavity where it will become firmly implanted in the bone cement. Wiping of the polymer pre-coat with methyl methacrylate monomer will dissolve some of the surface of the polymer and thus foster a good interfacial bond between the old cement and the new cement.

Polymerization of the bone cement composition is exothermic and generates in vivo temperatures of around 60° C., which can lead to necrosis of the surrounding bone tissue. Likewise, methyl methacrylate monomer is toxic substance and adversely affects the patient systemic. According to the techniques of the present invention, if one utilizes a pre-coated prosthesis, which is preferred, a lesser amount of new bone cement is employed during the surgical procedure. The exotherm of the reaction is thus lessened, decreasing the probability of necrosis and the lesser amount of toxic monomer decreases the probability of systemic interference.

Under normal conditions, once the components of the bone cement are mixed and forced into the prepared bone cavity, polymerization has begun and a state of curing of the polymer is reached in approximately two to five minutes where further manipulation of the implant becomes difficult. Hence, there is very little time during the operative procedure for proper positioning and location of the prosthesis within the bone cavity. Moreover, after positioning of the prosthesis and sufficient polymerization of the bone cement to secure the prosthesis, subsequent removal of the prosthesis for repositioning or replacement requires a further reaming of the bone cavity to remove the old polymerized bone cement. Since the actual reaming of the bone to provide the implant cavity may possibly damage the bone tissue, proper initial location of the prosthesis is particularly important. Should the prosthesis make contact with the inner surface of the bone cavity without a bone cement buffer therebetween, later physical movement is subject to pain and will cause necrocis of the bone. Abraded particulate bone matter if it becomes free within the bone cavity, may lead to early failure of the implant.

In accordance with the process of my previously described United States Letters Patent, if desired to also achieve the advantage of that invention, the prosthesis itself may be pre-coated with bone cement in a substantially uniform manner in order to enhance further the bonding between the prosthesis and the cement. In the preferred practice of this invention, it is contemplated that my earlier invention could also be employed along with the delivery system of the present invention.

In accordance with the process of this invention after the orthopedic surgeon has prepared the bed, or in more laymen terms, the cavity of the bone in which the implant will be inserted, a mixture of the bone cement composition and resorbable particles is first inserted and the prepared bed is lined with this mixture. The composition may comprise from about 5% to about 50% by weight of resorbable particles, preferably from about 25% to about 35% by weight of resorbable particles, and most preferably, about 30% by weight of resorbable particles so that particle to particle contacts can be achieved. The resorbable particles may be any of a common list known to those skilled in the art, but basically may be selected from the group consisting of allogeneic or heterogenic whole bone, demineralized bone, or deproteinized bone, bone morphogenic proteins, collagen, gelatin, polysaccharides, polylactic and polyglycolic acid, polyorthoester, calcium phosphate compounds such as TCP (tricalcium phosphate) and hydroxyapatites, or any other biocompatible and resorbable compounds.

The thickness of this lining may be from about 0.5 mm to about 5 mm in thickness. In most typical operations, the resorbable particle bonding cement mixture is delivered into the prepared bed as a liner by pressurized injection gun, again, commonly known to those skilled in the art. Thereafter, prepared bone cement in substantially pure form, is also injected into the prepared bed or bone cavity so that it substantially fills the remainder of the cavity. Next the prosthesis is placed into the prepared bone cement bed.

Figure 1B:
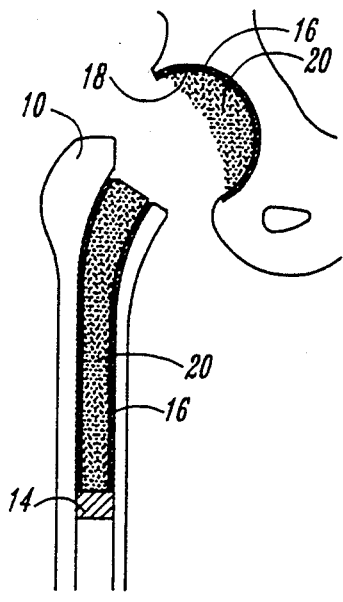
Figure 1C:
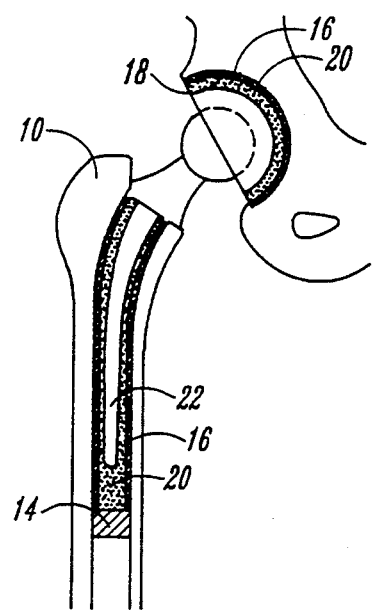

FIGS. 1a, 1b and 1c illustrate the process just described in conjunction with total hip replacement.

As illustrated in FIG. 1a, the femur (10) is drilled out to provide a prepared bed (12). The bed (12) has a cement plug (14) at the bottom. Thereafter bed (12) is lined with a resorbable particle layer (16), in the manner previously described. The resorbable particle layer (16) typically would contain 30% resorbable particles and the rest bone cement as hereinbefore described. In like manner, the prepared surface of the acetabular socket (18) is also so lined. Thereafter, a second injection Gun (21) is utilized (see FIG. 3b) to fill the remaining portion of the prepared bed with substantially pure bone cement (20). Next the femoral prosthesis (22) is inserted (FIG. 1c) and positioned properly by the orthopedic surgeon, just prior to closure. In time, resorbable particles (24) will Gradually be absorbed by the body and replaced by similarly positioned new bone tissue ingrowth. As a result, the amount of the surface between the bone cement and the bone is increased and the strength of the bond is increased by the natural bonding that occurs between new bone growth and the bone cement (see FIGS. 4a and 4b).

In summary, the method of delivery described in 1a, 1b and 1c, is as follows;
(1) The resorbable particles are loaded into a delivery gun and placed onto the surface of the prepared bone surfaces about 0.5–5 mm thickness.
(2) The pure bone cement is then injected into the prepared bone particle surfaces using the cement injection gun.
(3) The prosthesis is placed into the prepared bone cement bed.

This sequence of the operation is shown schematically in FIG. 1a, 1b and 1c.

Figure 2A:
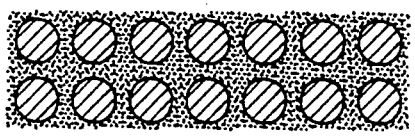
FIG. 2a and 2b show a schematic view of both a nonporous and a porous flexible, resorbable particle sheet which may be used to line the prepared bed.
Figure 2B:
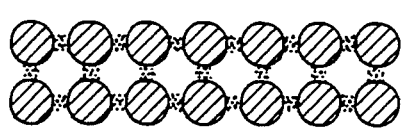

In another method of achieving the same result, resorbable particles are made into a flexible, porous, or nonporous sheet of a thickness within the range of about 1 mm to about 5 mm as illustrated in FIGS. 2A and 2B. This sheet is cut to size of the prepared bone surface area and placed therein by using an expandable device which would conform it to the irregular surface and contours of the prepared bed or cavity. Thereafter the bone cement is injected and the prosthesis inserted in the manner as previously described.

Yet another delivery system is illustrated in FIGS. 3a and 3b. There a precise template (13) (with bone cement delivering hole in the middle as shown in FIGS. 3A and 3B) undersized in comparison with the prepared bone bed is used. This template is placed in the cavity and the bone cement resorbable particle composition is introduced around the exterior of the template. Thereafter, the substantially pure bone cement is introduced through the end of the template, while gradually withdrawing the template (see FIG. 3b). In this manner the delivery is again achieved.

Regardless of which of these systems are used, the result is as illustrated in FIGS. 4a and 4b, namely, the prostheses has at its interface, substantially pure bone cement and correspondingly, the bone has at its interface a layer of composition mixture that is comprised of bone cement and resorbable particles, which eventually are resorbed and replaced with new bone ingrowth. As a result, the interface materials (particles) are resorbed and replaced with new tissues; the interfacial strength is increased due to the stronger new bone tissue, and a more viable interface between the bone and cement will result. Numerous advantages are achieved, namely:
(1) Immediate fixation of implants similar to the bone cement fixation;
(2) Tissue ingrowth into the resorbed space will result in a viable fixation of the implant similar to the porous surfaced implants. If not resorbed the material will act as load carrying member at the interface between bone and cement; and
(3) Less likelihood of resorption of the ingrown bony tissues due to the less rigid PMMA compared to metallic beads inducing more deformation for a given body load resulting in stimulation of the newly ingrown tissues.

It is of course also true that the process requires some extra manufacturing and surgical operations which must be performed by a skilled orthopedic surgeon in a small period of time. Moreover, the process should probably not be used with patients whose patient profile indicates an unlikely production of substantial new bone tissue. The following example is offered to illustrate, but not limit, the process of the present invention.

EXAMPLE

Canine femora were osteotomized through base of lesser trochanter at a right angle to the long axis. The intramedullary cavity was drilled and reamed to a diameter of 10 mm, with a depth of 11 cm. The cavity was irrigated with saline solution. The PMMA tube was filled with either bone cement or bone mineral particle impregnated bone cement and a 4 mm diameter, 10 cm long stainless steel rod was inserted. After the cement had cured four hours bone mineral particles were mixed thoroughly with the powder portion of a commercially available PMMA bone cement (Zimmer, USA, Warsaw, Ind.). The standard powder to monomer ratio (2:1) was maintained. The mixture was stirred for 2 minutes and the dough was kneaded for an additional 2 minutes. The meduallary canal was then filled with the bone mineral particle impregnated bone cement (10%, 20%, 30%), and the PMMA tube was inserted.

Mechanical push-out tests of the prepared specimens were performed at room temperature. Interfacial shear strength between PMMA tube and bone cement/prosthesis and bone cement/bone and bone cement were determined by mechanical "push-out" test on a hydraulically controlled material testing machine (MTS Model 812, Minneapolis, Minn.). There was very little clearance between plunger and supporter.

Average values of shear strength between PMMA tube and bone cement, prosthesis (stainless steel rod) and bone cement, and bone and bone cement are given in Table 1. As can be seen the interfacial shear strength decreases with increasing amount of bone particles almost linearly. However, the shear strength between PMMA tube and bone, and between the PMMA tube and bone mineral particle impregnated bone cement are very high in comparison to the prosthesis and bone cement or bone and bone cement interfaces. Therefore, the possibility of occurrence of loosening between the PMMA tube and bone cement would not be high. Of course, the true interfacial strength between bone and bone cement can only be meaningful when obtained in vivo study which we are planning to undertake.

TABLE 1

Summary of mechanical push-out tests measuring the maximum interfacial shear strength

| Amount of bone particle (wt %) | Interfacial strength (MPa) of cement with | | |
|---|---|---|---|
| | bone | prosthesis | PMMA tube |
| 0 | 2.7 ± 0.8 | 13.2 ± 2.3 | 37.7 ± 2.4 |
| 10 | 2.2 ± 0.7 | 9.6 ± 1.7 | 35.8 ± 4 |
| 20 | 2.3 ± 0.6 | 7.9 ± 2.4 | 29.6 ± 3.4 |
| 30 | 1.7 ± 0.7 | 5.7 ± 1.9 | 21.5 ± 1.1 |

The invention accomplishes at least all of its stated objectives, as evidenced by the example.

What is claimed is:

1. In the process of orthopedic implantation of a prosthetic device in a prepared bed of a bone cavity having a surface readied to receive a prosthesis to be fixed in to said bone cavity by a bone cement composition, the improvement comprising:

forming a pre-coat on substantially all of the surface of the prepared bed of said bone cavity with a mixture of bone cement composition and resorbable particles to form a resorbable particle layer; and wherein said pre-coat has a predetermined thickness; and thereafter, inserting within the pre-coated bed a substantially pure bone cement composition thereby forming a fully prepared bone cement composition bed; and thereafter, positioning the prosthesis into the fully prepared bone cement composition bed.

2. The process of claim 1 wherein the pre-coating mixture of bone cement composition and resorbable particles is from about 5% to about 50% by weight of resorbable particles.

3. The process of claim 2 wherein the pre-coating composition is from about 25% to about 35% by weight of resorbable particles, wherein said particles are in contact with each other.

4. The process of claim 3 wherein the resorbable particles are selected from the group consisting of allogeneic whole bone, heterogenic whole bone, demineralized bone, deproteinized bone morphogenic proteins, collagen, gelatin, polysaccharides, polylactic and polyglycolic acid, polyorthoester, calcium phosphate compounds such as tricalcium phosphate hydroxyapatites, and any other biocompatible and resorbable compounds.

5. The process of claim 4 wherein the resorbable particles are demineralized bone.

6. The process of claim 1 wherein the thickness of precoat is from about 0.5 mm to about 5 mm.

7. The process of claim 1 wherein the particle size of resorbable particles is from 0.01 mm to 1.0 mm diameter.

8. The process of claim 1 wherein the polymer coating and the bone cement composition comprise acrylics.

9. The process of claim 8 wherein said acrylic comprises polymethylmethacrylate.

10. The process of claim 1 wherein said pure bone cement composition comprises a mixture of an acrylic polymer, an acrylic monomer, a catalyst, and an accelerator.

11. The process of claim 10 wherein said acrylic polymer is polymethylmethacrylate and said acrylic monomer is methylmethacrylate.

12. The process of claim 10 wherein said acrylic polymer is a mixture of polymethylmethacrylate and methylmethacrylate-styrene copolymer and said acrylic monomer is methylmethacrylate.

* * * * *